United States Patent
Baudino et al.

(10) Patent No.: US 10,445,463 B2
(45) Date of Patent: Oct. 15, 2019

(54) HEALTH BOOTH

(75) Inventors: Franck Baudino, Neuilly sur Seine (FR); Laurent Baudino, Paris (FR)

(73) Assignee: H4D INTERNATIONAL S.A., Luxembourg (LU)

( * ) Notice: Subject to any disclaimer, the term of this patent is extended or adjusted under 35 U.S.C. 154(b) by 361 days.

(21) Appl. No.: 12/677,351

(22) PCT Filed: Sep. 11, 2007

(86) PCT No.: PCT/FR2007/051906
§ 371 (c)(1),
(2), (4) Date: May 30, 2010

(87) PCT Pub. No.: WO2009/034238
PCT Pub. Date: Mar. 19, 2009

(65) Prior Publication Data
US 2010/0286492 A1 Nov. 11, 2010

(51) Int. Cl.
*A61B 5/00* (2006.01)
*G06F 19/00* (2018.01)
*G16H 50/80* (2018.01)

(52) U.S. Cl.
CPC ............ *G06F 19/34* (2013.01); *A61B 5/0002* (2013.01); *A61B 5/6888* (2013.01); *G16H 50/80* (2018.01); *A61B 2560/0242* (2013.01)

(58) Field of Classification Search
CPC .................................................. A61B 5/6888
See application file for complete search history.

(56) References Cited

U.S. PATENT DOCUMENTS

| | | | |
|---|---|---|---|
| 3,601,031 A * | 8/1971 | Abel et al. ..................... | 454/187 |
| 5,410,297 A | 4/1995 | Joseph et al. | |
| 5,415,176 A * | 5/1995 | Sato ..................... | A61B 5/0537 |
| | | | 177/245 |
| 5,448,991 A * | 9/1995 | Polson et al. ................. | 600/330 |
| 5,533,305 A * | 7/1996 | Bielecki ........................ | 52/79.1 |
| 5,544,649 A | 8/1996 | David | |
| 5,619,991 A | 4/1997 | Sloane | |
| 5,850,290 A * | 12/1998 | Horiguchi et al. ........... | 356/602 |
| 5,911,132 A | 6/1999 | Sloane | |

(Continued)

FOREIGN PATENT DOCUMENTS

| | | |
|---|---|---|
| DE | 4439080 A1 | 5/1996 |
| FR | 2462584 | 2/1981 |
| FR | 2588645 A1 | 4/1987 |

OTHER PUBLICATIONS

Vishay "Ambient Light and Electromagnetic Interference" Sep. 20, 2006 (document is attached).*

(Continued)

*Primary Examiner* — Niketa I Patel
*Assistant Examiner* — Shirley X Jian
(74) *Attorney, Agent, or Firm* — Hamre, Schumann, Mueller & Larson, P.C.

(57) ABSTRACT

A health booth (10) includes a shell (20), at least one chair (30), and at least one measurement arrangement (31, 32, 33, 34) for measuring data relative to the health of a user. The booth includes: a determination apparatus (41-50) for determining, at the time of taking a measurement, at least one condition under which said measurement is taken; and a storage device for storing the measurement results in a data structure together with said condition.

21 Claims, 2 Drawing Sheets

(56) References Cited

U.S. PATENT DOCUMENTS

| | | | |
|---|---|---|---|
| 5,938,594 A | 8/1999 | Poon et al. | |
| 6,205,716 B1* | 3/2001 | Peltz | E04H 1/125 |
| | | | 345/905 |
| 6,238,337 B1 | 5/2001 | Kambhatla et al. | |
| 6,308,466 B1* | 10/2001 | Moriarty | 52/79.5 |
| 6,345,195 B1* | 2/2002 | Herskowits | A61B 5/0064 |
| | | | 600/473 |
| 6,428,124 B1* | 8/2002 | Bluth et al. | 312/194 |
| 6,468,210 B1 | 10/2002 | Iliff | |
| 6,475,143 B2 | 11/2002 | Iliff | |
| 6,511,435 B1* | 1/2003 | Bluth et al. | 600/490 |
| 6,524,241 B2 | 2/2003 | Iliff | |
| 6,527,713 B2 | 3/2003 | Iliff | |
| 6,569,093 B2 | 5/2003 | Iliff | |
| 6,692,436 B1* | 2/2004 | Bluth et al. | 600/300 |
| 6,888,640 B2* | 5/2005 | Spina et al. | 356/601 |
| 6,942,625 B1* | 9/2005 | Bryant | 600/538 |
| 7,024,370 B2 | 4/2006 | Epler et al. | |
| 7,038,588 B2* | 5/2006 | Boone et al. | 340/573.1 |
| 7,149,756 B1 | 12/2006 | Schmitt et al. | |
| 7,230,819 B2* | 6/2007 | Muchow | F03D 9/007 |
| | | | 307/22 |
| 8,160,836 B2 | 4/2012 | Pompei et al. | |
| 8,577,642 B2 | 11/2013 | Pompei et al. | |
| 8,647,270 B2* | 2/2014 | LeBoeuf et al. | 600/301 |
| 9,152,769 B2* | 10/2015 | Baudino et al. | |
| 10,219,734 B2* | 3/2019 | Williams | A61B 5/222 |
| 2001/0025226 A1* | 9/2001 | Lavery | 702/108 |
| 2002/0002325 A1 | 1/2002 | Iliff | |
| 2002/0013515 A1 | 1/2002 | Iliff | |
| 2002/0196141 A1* | 12/2002 | Boone et al. | 340/540 |
| 2004/0124711 A1* | 7/2004 | Muchow | F03D 9/007 |
| | | | 307/64 |
| 2004/0125996 A1* | 7/2004 | Eddowes | A61B 5/0059 |
| | | | 382/128 |
| 2004/0260156 A1* | 12/2004 | David | A61B 5/0205 |
| | | | 600/300 |
| 2005/0101884 A1 | 5/2005 | Weeks | |
| 2005/0154264 A1* | 7/2005 | Lecompte et al. | 600/300 |
| 2005/0171451 A1* | 8/2005 | Yeo | A61B 5/1171 |
| | | | 600/547 |
| 2006/0047188 A1* | 3/2006 | Bohan | 600/300 |
| 2007/0167837 A1* | 7/2007 | Moyer et al. | 600/476 |
| 2008/0077436 A1* | 3/2008 | Muradia | 705/2 |
| 2008/0091470 A1* | 4/2008 | Muradia | 705/3 |
| 2009/0083066 A1* | 3/2009 | Bailey et al. | 705/2 |
| 2009/0167838 A1 | 7/2009 | Poisner et al. | 348/14.04 |
| 2009/0210280 A1* | 8/2009 | Jin et al. | 705/9 |
| 2009/0216142 A1* | 8/2009 | Stelzer et al. | 600/509 |
| 2010/0179389 A1* | 7/2010 | Moroney, III | G06F 19/3406 |
| | | | 600/301 |
| 2014/0276276 A1* | 9/2014 | Kurosawa | 601/89 |

OTHER PUBLICATIONS

International Search Report in PCT/FR2007/051906, dated Jun. 10, 2008.

Written Opinion of ISA in PCT/FR2007/051906, dated Jun. 10, 2008.

\* cited by examiner

HEALTH BOOTH

BACKGROUND OF THE INVENTION

The invention relates to a health booth for obtaining measurements establishing the health of a user or of a population.

Establishing a person's health requires a number of measurements (weight, heart rate, temperature, etc.) to be taken under the supervision of medical personnel.

These measurements must sometimes be repeated at regular intervals to track how they change over time.

The obligatory presence of health personnel causes a number of problems.

First of all, it is clear that in developing countries, where the density of health personnel is low, it is difficult to conduct a health campaign, especially in an emergency, where there is an epidemiological risk present.

In other regions, the main impediment to health screening individually or collectively on a large scale is the relatively high cost of the presence of the above-mentioned health personnel.

To limit the above-mentioned problems, there are known, in particular from the document U.S. Pat. No. 5,544,649, "telemedicine" methods in which patients communicate with a doctor or other health personnel remotely, via a telecommunications network, the patients themselves effecting a number of measurements that are sent to the doctor via the network.

It should be noted that those solutions are not really satisfactory since they require the presence of health personnel when the measurements are taken, even though at a remote location.

One solution that springs naturally to mind would be to have patients take the measurements themselves, for example at home, with no contact with medical personnel, and then send the measurements to a remote center for subsequent processing.

However, it is difficult to envisage such a procedure since it is known that medical measurements are strongly linked to the conditions under which they are taken, in particular the patient's stress or fatigue and the meteorological, sound, and light environment at the time of taking the measurements.

In other words, if this information is not known, the measurements cannot be used by a doctor with sufficient reliability.

OBJECT AND SUMMARY OF THE INVENTION

The present invention mainly aims to solve the above drawbacks.

To this end, the invention relates to a health booth including a shell, at least one chair, and at least one measurement means for measuring data relative to the health of a user. This booth includes:
  determination means for determining, at the time of taking a measurement, at least one condition under which the measurement is taken; and
  storage means for storing the measurement results in a data structure together with said condition.

In the context of the invention, the expression "health booth" must be interpreted broadly, and designates any space defined by a shell in which users can themselves make a number of measurements relating to their health without the presence of medical personnel being necessary, even at a remote location.

A health booth in the sense of the invention can be transportable, for example, so that it can be installed temporarily at a given location. Health booths in the context of the invention can in particular consist of mobile homes or vehicles of the type used for collecting blood from donors.

A health booth in the context of the invention can also consist of a fixed structure intended to be installed in places through which people pass, for example airports or hotels.

The difference between the health booths of the invention and the previously-known installations lies in the fact that the environmental conditions, at the time of taking a measurement, are stored in a data structure together with the measurement results.

Thus, when health personnel is informed of the measurement results, said personnel is fully aware of the conditions under which said measurements were taken, thus making said data fully useable.

In an embodiment of the invention, said determination means are suitable for measuring at least one data item from among the following:
  a position of the user;
  the temperature inside and/or outside the shell;
  a sound level inside and/or outside the shell;
  a humidity content inside and/or outside the shell; and
  a brightness level inside and/or outside the shell.

Indeed, it is known that the following data items are necessary for good interpretation of at least one medical measurement.

In particular, the position of the user greatly influences the measured blood pressure. It is recommended that blood pressure is measured in a seated position, the arm resting on a table and the inflatable cuff positioned on that arm at the same level as the heart.

It is also known that the measured blood pressure is greatly influenced by events liable to increase it, in particular cold, noise, and physical effort.

It is also known that environmental stress and hyperthermia greatly influence the heart rate.

It is also known that the blood oxygen saturation level is greatly influenced by the ambient light level and by the relative humidity to which the skin is exposed.

Generally speaking, the means for measuring the above data can consist of appropriate sensors combined with calculation means.

For example, to be sure that a user is seated comfortably when taking blood pressure, it can be envisaged to use pressure sensors placed on the seat and on the backrest of the chair in the health booth.

To be sure that the user's arm is resting in an appropriate position, sensors can be placed on an armrest of the chair in the health booth.

A thermometer, a microphone, a hygrometer, and a photoelectric cell can be used to measure the temperature, sound level, relative humidity and brightness inside or outside the shell.

In a preferred embodiment, the health booth includes means for verifying that health measurements are taken when a given condition satisfies at least one predetermined criterion.

This feature means that health measurements can be effected under optimum conditions.

For example, it can be decided not to measure blood pressure until the patient has been seated for at least five minutes.

In one embodiment of the invention, these control means are optional because it can be important, especially after a natural disaster, to take large numbers of health measurements, in order to implement emergency measures, even though the measurement conditions are below optimum.

In other embodiments, the control means can be used systematically.

In a preferred embodiment, the shell of the health booth of the invention includes at least one opening for linking the health booth to at least one other health booth.

This forms a "hospital" consisting of interconnected health booths.

This feature proves particularly advantageous for guaranteeing certain predetermined conditions in a number of health booths installed in the same area.

For example, in a particularly hot region, it is easier to reduce the temperature in a number of health booths that communicate with each other than in the same number of individual health booths.

The health booth according to the invention includes means for sending the data structure to a remote center.

Advantageously, this feature makes it easier to collect the data structures as recorded in a plurality of health booths or in a hospital within the meaning of the invention.

In a particular embodiment, the health booth of the invention includes power supply means.

These power supply means can use solar energy, for example, or open and/or closed thermodynamic cycles. They are used to supply the health booth with electricity and to regulate the temperature inside the health booth.

For more details of such power supply means, the person skilled in the art can refer to the patent documents FR 2 462 584 and FR 2 588 645.

BRIEF DESCRIPTION OF THE DRAWINGS

Other features and advantages of the present invention emerge from the following description with reference to the drawings, which show a non-limiting embodiment of the invention, and from appendix 1. In the figures.

DETAILED DESCRIPTION OF ONE EMBODIMENT

Figure 1:
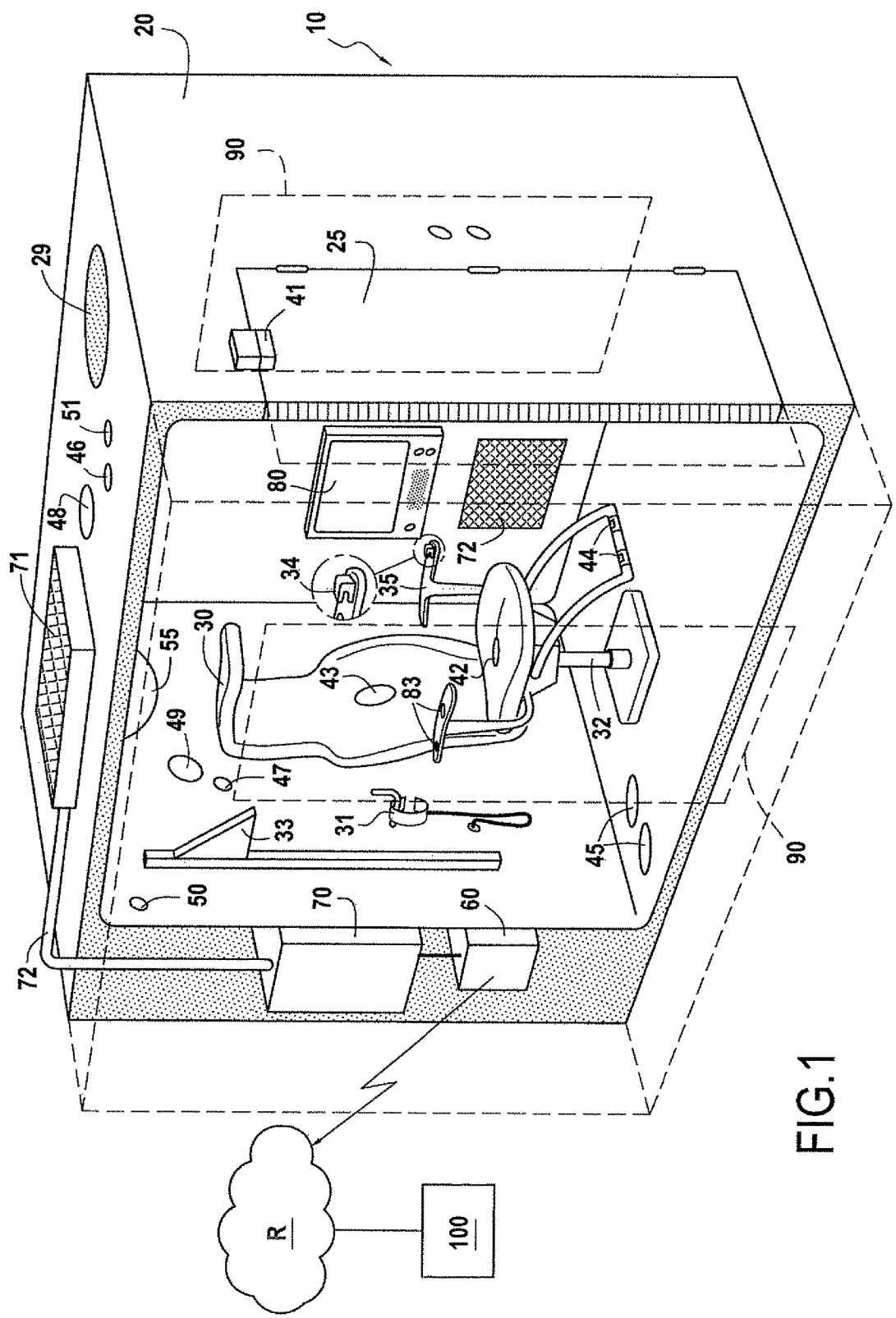
FIG. 1 represents a health booth conforming to one particular embodiment of the invention.

FIG. 1 represents a health booth 10 conforming to one particular embodiment of the invention.

The main components of the health booth 10 are a shell 20 and a chair 30.

In a different embodiment of the invention, the health booth 10 can contain a number of chairs 30. The health booth 10 includes a number of means for measuring data related to a user's health.

In the embodiment described here, these measuring means comprise:
 an inflatable cuff 31 placed on the user's arm to measure their blood pressure, this cuff further including heart rate sensors, not shown;
 scales 32 for measuring the user's weight when seated on the chair 30;
 a height gauge 33 for measuring the user's height in a standing position; and
 an oximeter 34 for measuring the user's blood oxygen saturation level.

In the embodiment described here, the oximeter 34 is fixed to the end of one armrest 35 of the chair 30.

According to the invention, the health booth 10 includes a number of sensors for determining the conditions under which the health measurements are taken.

In the embodiment described here, these sensors comprise:
 a sensor 41 for determining whether the door 25 of the health booth is open or closed;
 a pressure sensor 42 on the seat of the chair 30 for detecting whether the user is seated on the chair;
 a pressure sensor 43 in the back rest of the chair 30 for determining whether the user is sitting back in the chair 30;
 two sensors 44 on a footrest attached to the chair 30 for detecting whether the user has both feet resting on the footrest;
 two sensors 45 disposed under the height gauge 33 to determine whether the user is correctly placed when measuring their height with the height gauge 33 or measuring their blood pressure in the standing position using the inflatable cuff 31;
 a thermometer 46 for measuring the temperature outside the shell 20;
 a thermometer 47 for measuring the temperature inside the shell 20;
 a hygrometer 48 for measuring the relative humidity outside the shell 20;
 a hygrometer 53 for measuring the relative humidity inside the shell 20;
 a microphone 50 for measuring the sound level inside the health booth 10; and
 a photo-electric cell 54 for measuring the brightness level outside the shell 20.

In the embodiment described here, the health booth 10 includes a lamp 55 for producing a predetermined brightness inside the health booth 10 so that the brightness inside the shell 20 is the optimum for taking health measurements with the door 25 closed.

In accordance with the invention, when a health measurement is taken, the conditions under which it was taken are stored in a data structure together with the measurement results.

In the example described here, this data structure is a computer file.

Figure 2:
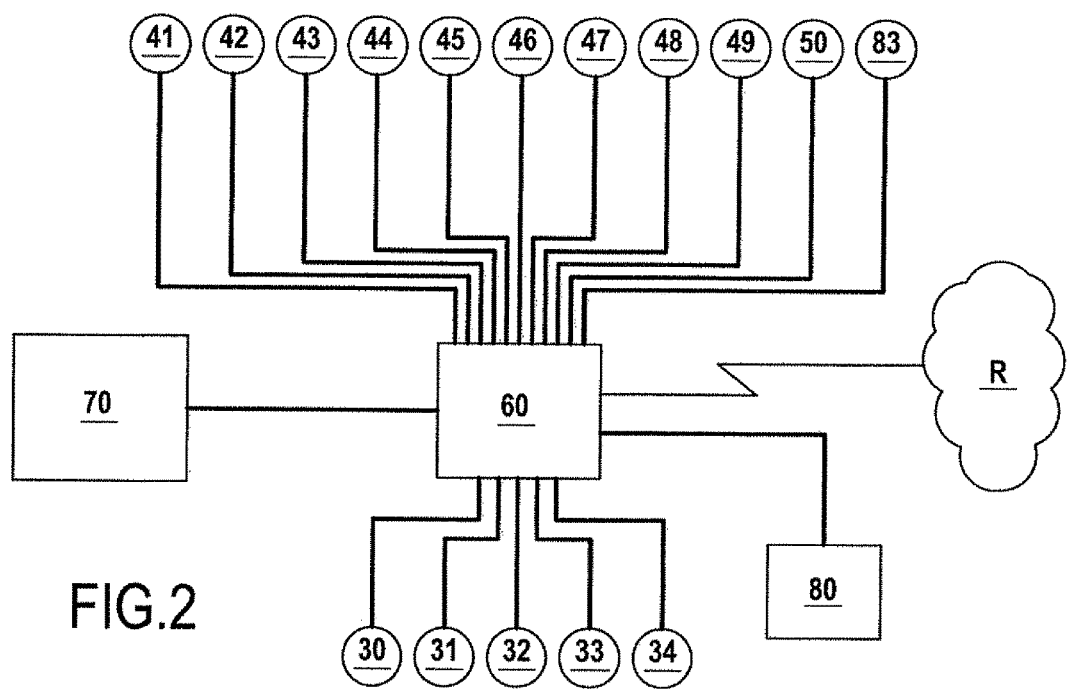
FIG. 2 shows the connections of a computer used in the FIG. 1 health booth.

The health booth 10 includes a computer 60 to which each of the sensors and measuring instruments referred to above is connected, as shown in FIG. 2.

This computer 60 is adapted to generate a file as shown in Appendix 1 and to send that file to a remote center 100 via a telecommunications network R.

In the example described here, the computer 100 is installed within the thickness of the shell 20.

In the particular embodiment described here, the computer 60 and all the electrical equipment of the health booth 10 are supplied with power by a motor 20 placed within the thickness of the shell 20 and connected to a solar panel 71.

The solar panel 71 heats a fluid injected into the motor 70 via a pipe 72, the motor using this heat energy to generate the electrical power supply necessary for the electric instruments of the health booth 10 to operate and to effect cooling by compressing another fluid.

The motor 70 is therefore adapted in particular to regulate the temperature inside the health booth 20 by injecting warm air into it via a grille 72.

The health booth 10 described here also includes a ventilation grille 29 and a touch-sensitive screen 80 for interaction with the user.

There is described below a scenario for use of the health booth 10 to establish a health file for a user in the form shown in Appendix 1.

The user enters the health booth 10 via the door 25, leaving the door open behind them, which is detected by the sensor 41.

The touch-sensitive screen 80 shows a message prompting the user to enter their age. In this embodiment the health measurements cannot begin until this data item is entered. The age is then stored in the Appendix 1 file.

Once the age of the user has been entered, a message on the touch-sensitive screen prompts the user to measure their height using the height gauge 33.

Until the user places their feet correctly on the marks aligned with the sensors 45, a message prompts them to assume a new position.

The height is then stored in the Appendix 1 file.

Once their height has been measured, the user is prompted to remain standing on the above-mentioned marks to measure their blood pressure in the standing position. Sensors in the cuff 31 detect that it is positioned correctly.

When this has been detected, the computer 60 starts a counter and takes two blood pressure measurements, after one minute and after five minutes, respectively, and the respective results 11.8 and 11.6 of these measurements are stored in the Appendix 1 file.

The user is then prompted to sit on the chair 30.

Before measuring their weight, it is verified that the user is seated (sensor 42 activated) with both feet placed on the footrest (position of the feet detected by the sensors 44).

If so, the weight is measured by the scales 32 and stored in the Appendix 1 file (81 kg).

A message on the touch-sensitive screen 80 then prompts the user to put the blood pressure cuff 31 on again to measure their blood pressure in the seated position.

In the embodiment described here, to optimize the blood pressure measurement, the user is required to be seated (this is detected by the sensor 42) and sitting back in the chair 30 (this is detected by the sensor 43) with their arm resting on the armrest 35 (this is detected by two position sensors 83).

When the computer 60 registers this position, it requests the user to wait for five minutes.

In this example, when the five minute delay expires, the user has unfortunately removed their arm from the armrest 35.

The measured blood pressure 12.7 is stored in the data structure, with information representing the fact that the user was seated and sitting back but that their arm was not positioned on the armrest.

At the time of measuring the user's heart rate using the blood pressure cuff 31, the microphone detects a very high noise level, namely a noise level of 120 dB caused by a jackhammer.

It is known that noise level strongly impacts on the heart rate.

Consequently, the touch-sensitive screen 80 prompts the user to close the door 25, which is detected automatically by the sensor 41.

A noise level of 50 dB is then measured inside the health booth 10.

When the door 25 is closed, the lamp 55 produces an optimum brightness level of 120 cd.

When the measurement is taken the temperature inside the health booth is 19° C.

The touch-sensitive screen 80 prompts the user to wait for one minute and a heart rate of 60 bpm is then stored in the Appendix 1 file.

Finally, a message prompts the user to measure their blood oxygen saturation by placing their index finger in the oximeter 34 positioned at the end of the armrest 35.

The measured brightness (120 cd) and relative humidity (4%) are stored with the result of this $SpO_2$ blood oxygen saturation measurement: 95%.

The computer 60 then sends the file automatically to a remote center 100 via a telecommunications network R.

In the embodiment described here, the health booth 10 has two facing removable doors 90.

Figure 3:
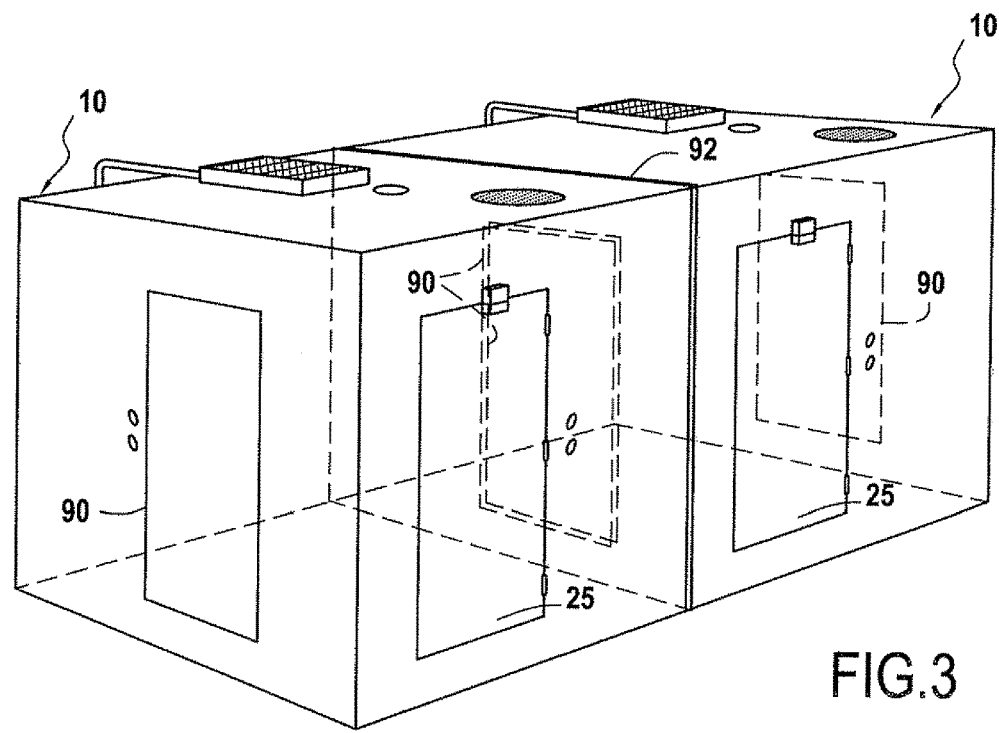
FIG. 3 shows a number of health booths of the invention interconnected to form a hospital; and Appendix 1 gives one example of a data structure generated by the FIG. 1 health booth.

As shown in FIG. 3, these doors enable a "hospital" to be produced by positioning two health booths side by side and removing the removable doors 90 to create an airlock passage between the two health booths.

In a preferred embodiment, the health booths 10 in this particular arrangement are connected together by an air-tight seal 92.

APPENDIX 1

| Age: | | 30 years |
|---|---|---|
| | Blood pressure | |
| Seated: | ☑ | 12.7 |
| Sitting back: | ☑ | |
| Arm on armrest: | ☐ | |
| Duration: | 5 min | |
| | STANDING: | |
| 1 min: | | 11.8 |
| 5 min: | | 11.6 |
| | Weight | |
| Seated: | ☑ | 81 kg |
| Feet on footrest: | ☑ | |
| Height: | | 178 cm |
| | Heart rate: | |
| T: | 19° C. | 60 bpm |
| Brightness: | 120 cd | |
| Noise level: | 50 dB | |
| 1 min | ☑ | |
| | Blood oxygen saturation | |
| Brightness: | 120 cd | $SpO_2$ 95% |
| Relative humidity: | 4% | |

The invention claimed is:

1. A health booth configured to allow a patient to conduct self-measurement of health data of the patient, the health booth comprising:
 a shell;
 a chair arranged inside the shell and configured to support the patient in a seated position;
 a first measurement device, arranged inside the shell, configured for the patient to measure by him/herself the health data;
 a second measurement device, arranged on the inside or outside of the shell, configured to measure, at the time of measurement of the health data, environmental condition data that affects the measured health data and interpretation of the measured-health data;
 a data storage that stores the health data and the environmental condition data together in a computer file; and
 a transmission system configured to send the computer file to a remote center for evaluation, wherein the second measurement device comprises a patient position sensor configured to measure a portion of the environmental condition data, the patient position sensor further configured to detect a standing position of the patient associated with measurement of health data that requires the patient to be standing during measurement of the health data.

2. The health booth according to claim 1, wherein the second measurement device further comprises at least one of: a thermometer to measure the temperature inside and/or outside the shell; a microphone to measure the sound level inside and/or outside the shell; a hygrometer to measure the humidity content inside and/or outside said shell; and a photo-electric cell to measure a brightness level inside and/or outside said shell.

3. The health booth according claim 1, wherein the shell further comprises at least one opening for connecting the health booth to at least one other health booth.

4. The health booth according to claim 1, wherein the first measurement device comprises a scale configured to measure the weight of the patient when the patient is seated on the chair.

5. The health booth according to claim 4, wherein the second measurement device includes at least one pressure sensor selected from:
a first pressure sensor placed on the seat of the chair,
a second pressure sensor placed on the backrest of the chair,
a third pressure sensor placed on an armrest of the chair, and
a fourth pressure sensor placed on a footrest attached to the chair,
said at least one pressure sensor being configured to determine whether the patient is present in the chair and properly positioned for the weight measurement.

6. The health booth according to claim 1, wherein the first measurement device comprises an inflatable cuff configured to measure blood pressure of the patient, the cuff further including heart rate sensors and being configured to take measurements when the patient is standing or seated in the chair.

7. The health booth according to claim 1, wherein the first measurement device comprises a height gauge configured to measure the height of the patient in a standing position, and the second measurement device comprises two sensors disposed under the height gauge to determine whether the patient is correctly positioned with respect to the height gauge.

8. The health booth according to claim 1, wherein the first measurement device comprises an oximeter for measuring the blood oxygen saturation level of the patient, the oximeter being fixed to one end of an armrest of the chair.

9. The health booth according to claim 1, further comprising a touch-sensitive screen for interaction with the patient.

10. The health booth according to claim 1, further comprising a solar panel arranged on the outside of the shell and connected to a motor configured to run electrical equipment of the health booth.

11. The health booth according to claim 10, wherein the motor is positioned within the thickness of the shell.

12. The health booth according to claim 10, wherein the solar panel heats a fluid injected into the motor via a pipe, the motor using the heat energy of the fluid to regulate the temperature inside the health booth.

13. The health booth according to claim 1, wherein the shell comprises a closable door, and the second measurement device comprises a sensor for determining whether the door is open or closed.

14. The health booth according to claim 13, wherein the health booth further comprises a lamp for producing a predetermined brightness inside the health booth when the door is closed.

15. The health booth according to claim 1, wherein the health booth further comprises a computer to which the first and second measurement devices are connected, the computer comprising the data storage and the transmission system.

16. The health booth according to claim 15, wherein the computer is positioned within the thickness of the shell.

17. The health booth according to claim 9, wherein the touch-sensitive screen is mounted on the inside of the shell.

18. The health booth according to claim 17, wherein the touch-sensitive screen is in communication with the second measurement device, is configured to receive information from the second measurement device, and is configured to instruct the patient for proper measurement of the health data of the patient using the first measurement device.

19. The health booth according to claim 17, wherein the health booth is in a form of a vehicle.

20. A method of enabling self-measurement of health data by a patient in a health booth, the health booth comprising a shell, a chair arranged in the shell configured to support the patient in a seated position, a first measurement device arranged inside the shell, a second measurement device arranged on the inside or outside of the shell, a data storage, and a transmission system, the method comprising:
measuring, by the first measurement device, health data of the patient, said measuring being performed at the direction and control of the patient, without guidance from a third party at the time of measurement;
at the time of said measuring of the health data, measuring, by the second measurement device, environmental condition data that affects the measured health data and interpretation of the measured health data;
storing, by the data storage, the health data and the environmental condition data together in a computer file; and
transmitting, by the transmission system, the computer file to a remote center for evaluation.

21. A health booth configured to allow a patient to conduct self-measurement of health data of the patient, the health booth comprising:
a shell;
a chair arranged inside the shell and configured to support the patient in a seated position;
a first measurement device, arranged inside the shell, configured for the patient to measure the health data without guidance from a third party at the time of measurement;
a second measurement device, arranged on the inside or outside of the shell, configured to measure, at the time of measurement of the health data, environmental condition data that affects the measured health data and interpretation of the measured health data;
a data storage that stores the health data and the environmental condition data together in a computer file; and
a transmission system configured to send the computer file to a remote center for evaluation,
wherein the second measurement device comprises a patient position sensor configured to measure a portion of the environmental condition data, the patient position sensor further configured, when the health data being measured requires the patient to be seated in the chair, to detect a seated position of the patient and determine whether the detected seated position is appropriate for measurement of the health data.

* * * * *